United States Patent
Power et al.

(10) Patent No.: US 7,912,655 B2
(45) Date of Patent: Mar. 22, 2011

(54) METER HAVING MULTI-LEVEL USER INTERFACE

(75) Inventors: Barry D. Power, Elkhart, IN (US); Jeffrey A Culver, Sylvania, OH (US)

(73) Assignee: Bayer HealthCare LLC, Tarrytown, NY (US)

( * ) Notice: Subject to any disclaimer, the term of this patent is extended or adjusted under 35 U.S.C. 154(b) by 391 days.

(21) Appl. No.: 11/989,881

(22) PCT Filed: Aug. 3, 2006

(86) PCT No.: PCT/US2006/030401
§ 371 (c)(1),
(2), (4) Date: Feb. 1, 2008

(87) PCT Pub. No.: WO2007/019289
PCT Pub. Date: Feb. 15, 2007

(65) Prior Publication Data
US 2009/0093972 A1   Apr. 9, 2009

Related U.S. Application Data (60) Provisional application No. 60/705,958, filed on Aug. 5, 2005.

(51) Int. Cl.
   *G01N 33/48* (2006.01)
   *G01N 33/50* (2006.01)
   *G01N 31/00* (2006.01)
(52) U.S. Cl. .......................... 702/23; 702/19
(58) Field of Classification Search ............... 702/23, 702/19
See application file for complete search history.

(56) References Cited

U.S. PATENT DOCUMENTS

| 4,763,117 A | 8/1988 | Blattner et al. |
| 5,307,263 A | 4/1994 | Brown |
| 5,365,935 A * | 11/1994 | Righter et al. ............... 600/523 |
| 5,997,475 A | 12/1999 | Bortz |
| 2003/0032190 A1 | 2/2003 | Brown et al. |
| 2003/0093437 A1* | 5/2003 | Gargi et al. ............... 707/104.1 |
| 2003/0211617 A1* | 11/2003 | Jones ............................ 436/14 |

FOREIGN PATENT DOCUMENTS

| EP | 1437674 | 7/2004 |
| WO | WO 2005/037095 | 4/2005 |

OTHER PUBLICATIONS

Cox, J.R., J. Hovgaard, Duftschmidt, K., "A New Generation Hand Held Identifier for Customs Applications," IAEA-CN-86-7P, dated May 1, 2004, pp. 149-151, 3 pages.
Safesun, "Safesun Personal Ultraviolet Light Meter," Mar. 28, 2005, 3 pages http://web.archive.org/web/20050328021232/http://www.healthchecksystems.com/safesun.
Written Opinion corresponding to International Patent Application No. PCT/US2006/030401, European Patent Office, dated Nov. 22, 2006, 7 pages.
International Search Report corresponding to International Patent Application No. PCT/US2006/030401, European Patent Office, dated Nov. 22, 2006, 4 pages.

* cited by examiner

*Primary Examiner* — Mohamed Charioui
*Assistant Examiner* — Janet L Suglo
(74) *Attorney, Agent, or Firm* — Nixon Peabody LLP (57) ABSTRACT

A meter adapted to determine and store an analyte concentration reading, in particular a glucose concentration reading, and including an interface having a plurality of predefined levels of user features. The predefined levels may be selected by a user based on the user's preferences, needs and abilities.

7 Claims, 6 Drawing Sheets

METER HAVING MULTI-LEVEL USER INTERFACE

CROSS-REFERENCE TO RELATED APPLICATION

This application claims priority to U.S. Provisional Application No. 60/705,958, filed on Aug. 5, 2005, which is incorporated by reference in its entirety.

FIELD OF THE INVENTION

The present invention relates generally to meters and methods of using the same, and more particularly, to a meter having a multi-level user interface that allows a user to select one of a plurality of predefined levels of user features.

BACKGROUND OF THE INVENTION

The quantitative determination of analytes in body fluids is of great importance in the diagnoses and maintenance of certain physiological abnormalities. For example, lactate, cholesterol, bilirubin and glucose should be monitored in certain individuals. In particular, determining glucose in body fluids is important to diabetic individuals who must frequently check the glucose concentration in their body fluids to regulate the glucose intake in their diets.

Diabetic individuals often test their blood glucose levels via a blood glucose meter. Some existing glucose meters are adapted to allow users to program certain features of the glucose meter. With these types of glucose meters, the user must have some knowledge of how to program the meter or must be able to read and understand often complex user instructions. Alternatively, some glucose meters are not adapted to receive user input and instead have pre-programmed features that do not allow a user to customize the glucose meter. It would be desirable to allow a user to easily customize the glucose meter.

SUMMARY OF THE INVENTION

A meter adapted to determine and store an analyte concentration reading is disclosed according to one embodiment of the present invention. The glucose meter includes a display adapted to display information to a user of the meter and an interface that controls the display for the user. The interface has a plurality of predefined levels of user features that are adapted to be selected by the user. The glucose meter further includes at least one user input mechanism adapted to allow the user to select one of the plurality of predefined levels of user features.

A method for using a meter is disclosed according to one embodiment of the present invention. The meter is adapted to determine and store an analyte concentration reading. The meter includes a display adapted to display information to a user. The method comprises the steps of displaying information on the display via a user interface having a plurality of predefined levels of user features. The method further comprises selecting one of the plurality of predefined levels and displaying the user features associated with the selected predefined level.

A meter adapted to determine and store an analyte concentration reading includes a display adapted to display information to a user of the meter and an interface that controls the display for the user. The interface has at least three predefined levels of user features that are adapted to be selected by the user The meter further includes at least one user input mechanism adapted to allow the user to select one of the at least three predefined levels of user features.

A method for using a meter adapted to determine and store an analyte concentration reading, in which the meter has a display adapted to display information to a user, includes the acts of displaying information on the display via a user interface having at least three predefined levels of user features, selecting one of the at least three predefined levels, and displaying the user features associated with the selected predefined level.

The above summary of the present invention is not intended to represent each embodiment, or every aspect, of the present invention. Additional features and benefits of the present invention are apparent from the detailed description, and figures set forth below.

DESCRIPTION OF ILLUSTRATED EMBODIMENTS

The present invention is directed to a meter that is adapted to determine and store an analyte concentration in a body fluid sample which is collected with a lancing device. Examples of the types of analytes which may be collected include glucose, lipid profiles (e.g., cholesterol, triglycerides, LDL and HDL), microalbumin, hemoglobin A1C, fructose, lactate, or bilirubin. It is contemplated that other analyte concentrations may also be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1A:
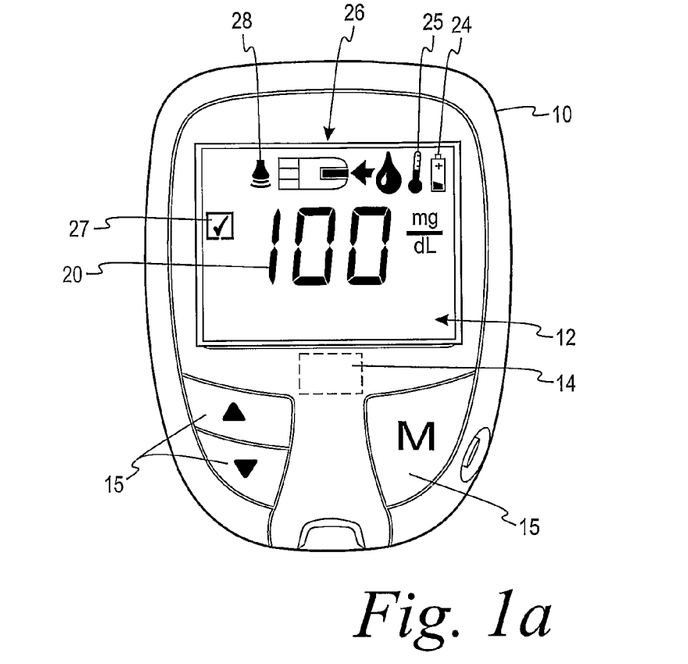
FIGS. 1a and 1b are front side views of a meter having a first predefined level of user features, according to one embodiment of the present invention.
Figure 1B:
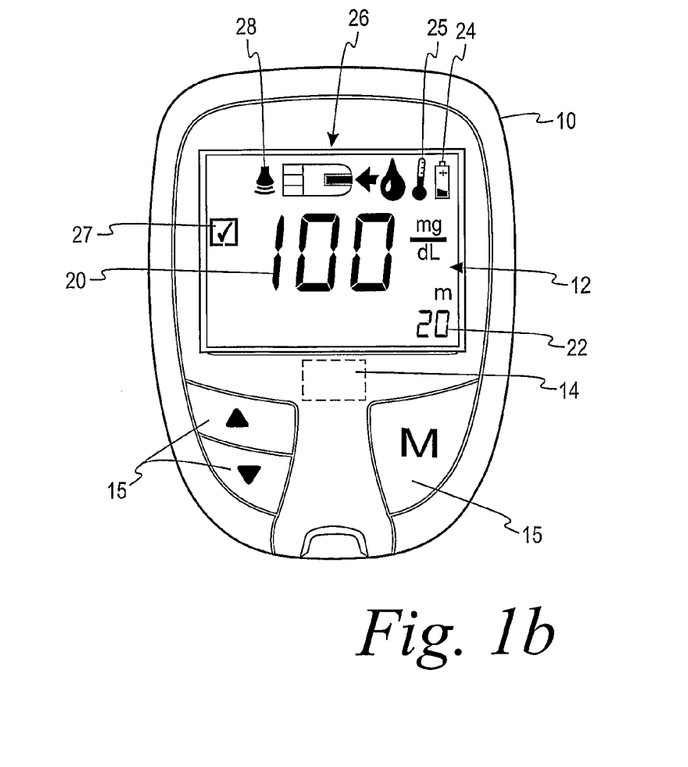

One embodiment of the present invention is a meter 10 as shown in FIGS. 1a and 1b. The meter 10 has a display 12 that is adapted to display information to a user of the meter 10. The meter 10 also has an interface 14 that controls the display 12 for the user. In some embodiments, the interface 14 has a plurality of predefined levels of user features that are adapted to be selected by the user. The meter 10 also has at least one user input mechanism 15 that is adapted to allow the user to select one of the plurality of predefined levels of user features. The user input mechanism 15 may include, for example, buttons, scroll bars, touch screens, or any combination of such items. The meter 10 may also have a memory device (not shown) that is adapted to store the selected predefined level. While the remainder of the disclosure herein will be directed towards a multi-level user interface for use in glucose meters, it is to be understood that it may be implemented in meters used for determining other analytes.

FIGS. 1a and 1b show meters having some user features that may be associated with one of the plurality of predefined levels. In one embodiment, one of the plurality of predefined levels may include user features that are relatively simple and easy to understand. This level may be selected by a user who has not previously used the meter 10 or by a user who does not require more sophisticated features, i.e., a "beginner" or "novice" mode. For example, the meter 10 in FIG. 1a includes a feature that displays a blood glucose concentration reading 20. The reading 20 includes a value associated with the blood glucose level as well as the units associated with that reading 20. In addition to the concentration reading 20, the meter 10 in FIG. 1b also displays a feature that allows a player to store a certain number of concentration readings 22. For example, in FIG. 1b at least twenty concentration readings 22 can be stored while a user is in this "beginner" mode. The concentration readings 22 may be stored in a memory device so that the user can retrieve the concentration readings 22 at a later time. This may be desirable so that a user can monitor his or her blood glucose readings over a period of several days. This feature, and other features, may be selected using the input mechanism 15. For example, the user may use the input mechanism 15 to display a list of features that are associated with one of the plurality of predefined levels. The user is able to scroll through the list of features and select a particular feature from the list.

It is contemplated that other user features may be available in a "beginner" mode in addition to the features listed herein. In certain embodiments, some of these features may be "standard" features that are also available in other modes, i.e., intermediate and advanced modes. For example, one such feature, shown in FIGS. 1a and 1b, notifies a user of a low battery and is identified on the display 12 with a low battery icon 24. Another feature may notify the user that the temperature of the meter 10 is out of the required range for operating the meter 10. This feature may be indicated by a thermometer icon 25.

Other features that may be available in the "beginner" mode, as well as in other modes, may notify the user to apply a sample to a test strip. This feature may be indicated by a sample and test strip icon 26. Additionally, a user may need to use a test strip to determine that the meter 10 is in proper working condition. The reading from the test strip can then be marked using a check mark icon 27. Alternatively or additionally, the check mark icon 27 may be automatically applied to the test strip concentration reading by the meter 10. In yet other embodiments, the meter 10 may include a buzzer or alarm that can be set by a user as a reminder to take a concentration reading 22. A buzzer icon 28 indicates that the buzzer or alarm has been set.

Figure 2A:
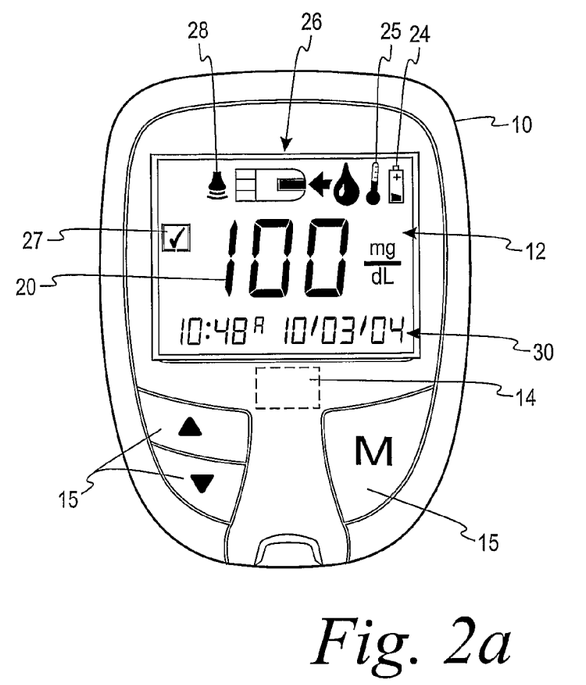
FIGS. 2a, 2b and 2c are front side views of a meter having a second predefined level of user features, according to another embodiment of the present invention.
Figure 2B:
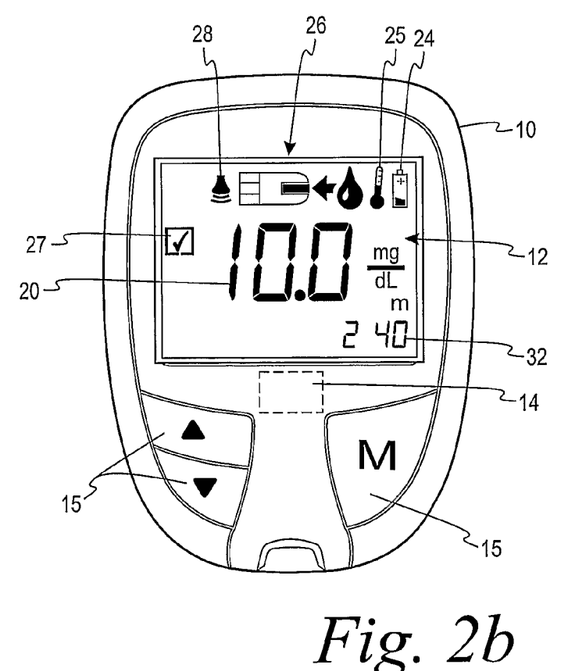
Figure 2C:
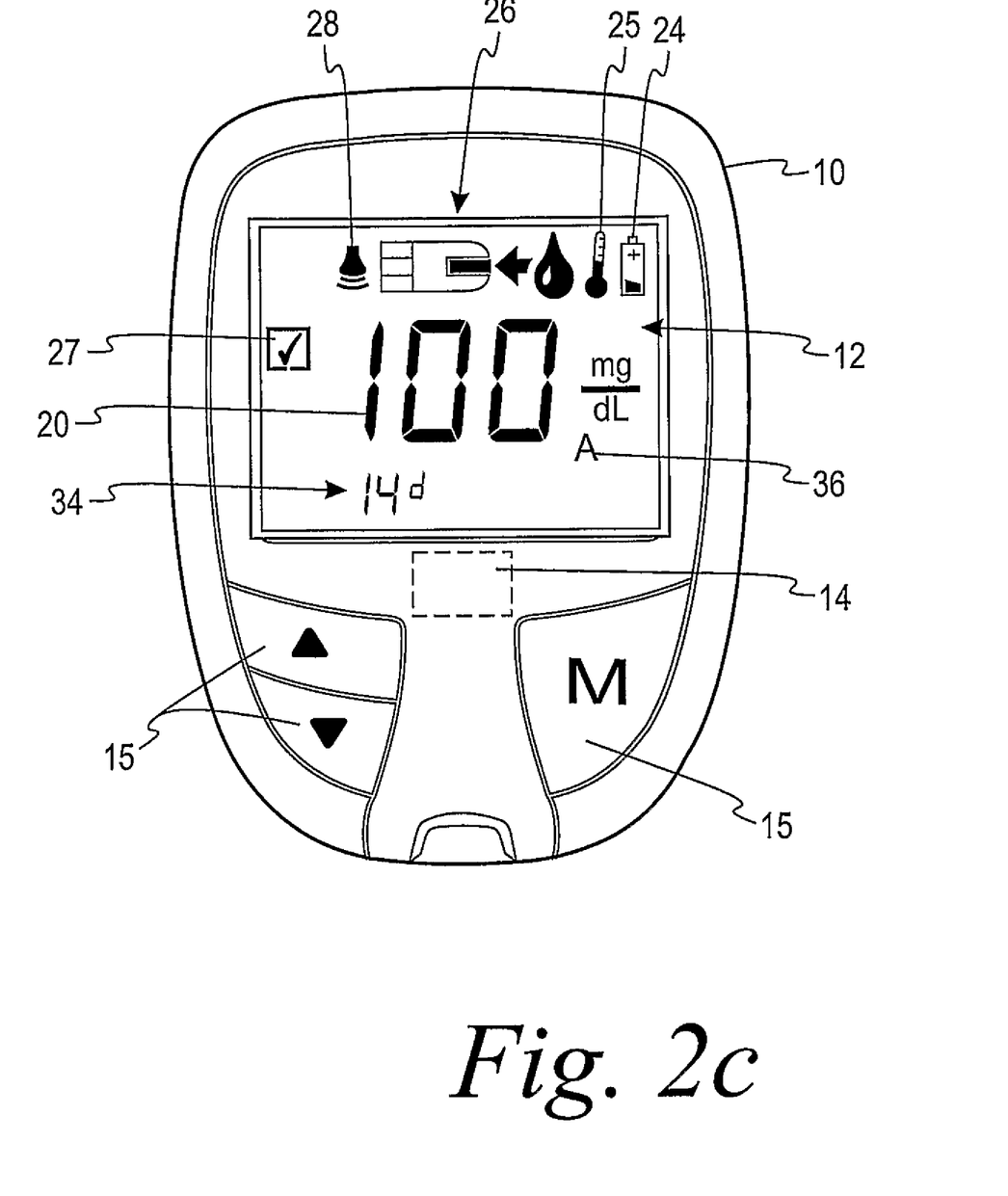
Figure 4:
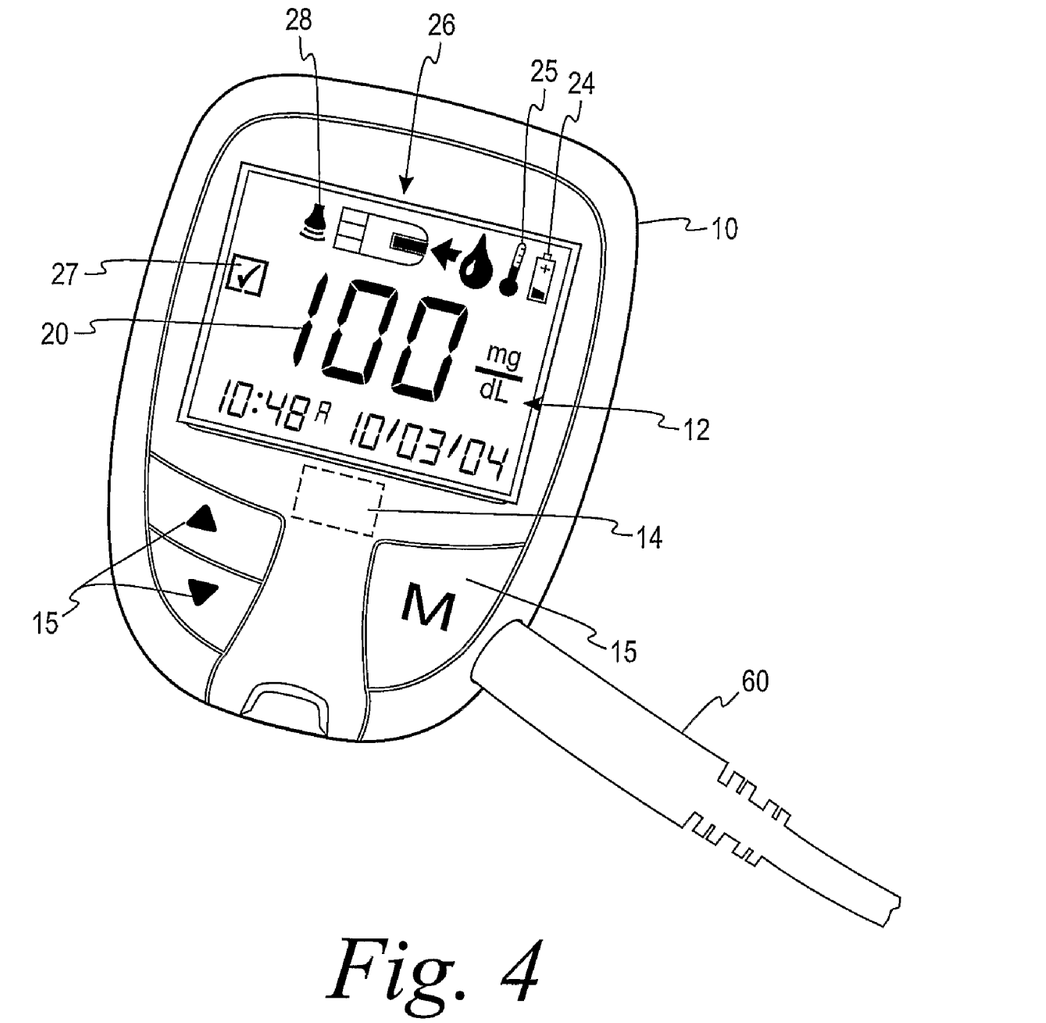
FIG. 4 is a front side view of a meter having a computer data interface.

In addition to storing a certain number of concentration readings, additional user features may be available. For instance, in another embodiment of the present invention, one of the plurality of predefined levels is adapted to display user features that are somewhat more sophisticated than the "beginner" level and includes features that are designed for more technically-knowledgeable users. As shown in FIGS. 2a, 2b and 2c, one such predefined level, which may be referred to as an "intermediate" level, may include features that offer more user options for storing and displaying concentration readings. For example, user features associated with an "intermediate" level may include, in addition to the blood glucose reading 20, a date and time indicator 30. Additionally, an "intermediate" level may also include a feature that allows a user to store a greater number of concentration readings 32. In some embodiments, at least 200 concentration readings 32 may be stored. For example, as shown in the embodiment in FIG. 2b, 240 readings may be stored. Other user features may allow a user to calculate a multi-day average 34 of concentration readings 32. For example, a 14-day average may be calculated as indicated in FIG. 2c. To indicate that the averaging feature is in use, an averaging icon 26, such as an "A", may be displayed on the meter 10. Furthermore, all of this information may be downloaded via a computer data interface 60 (see FIG. 4). These user features provide more ways of storing, displaying and calculating information that may be important to a user of the meter 10. In addition, doctors or other medical professionals may desire to have this information available to them as a way of monitoring the blood glucose levels of their patients.

It is contemplated that other user features may be available in an "intermediate" mode in addition to the features listed herein, such as one or more of the features described herein with respect to the "beginner" mode.

Figure 3A:
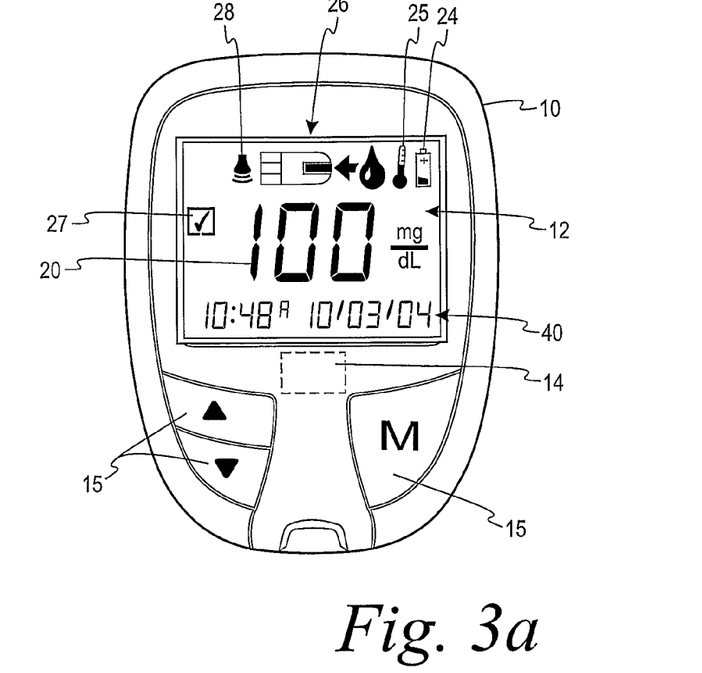
FIGS. 3a, 3b, 3c and 3d are front side views of a meter having a third predefined level of user features, according to a further embodiment of the present invention.
Figure 3B:
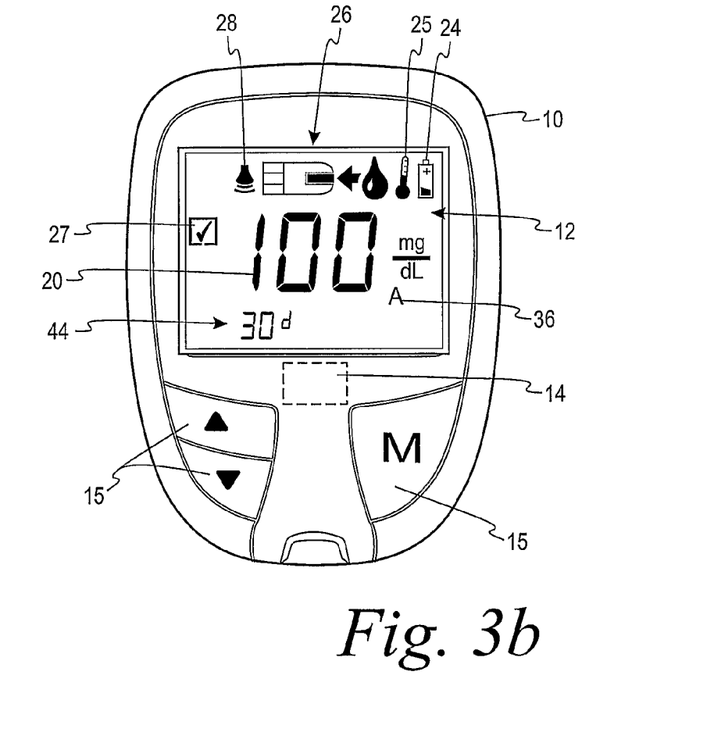
Figure 3C:
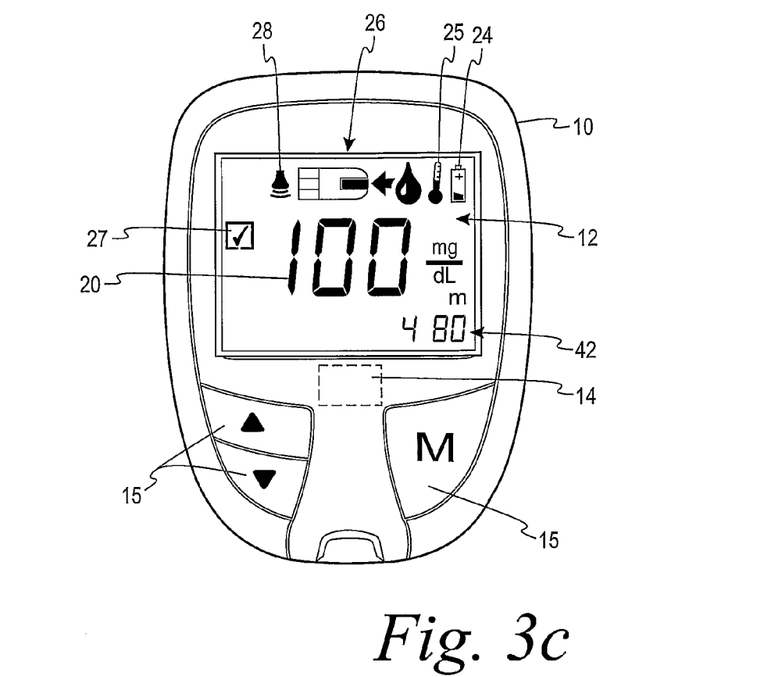

In addition to the "beginner" and "intermediate" levels described above, additional user features may be included in a third predefined level. This level, as depicted in FIGS. 3a, 3b, 3c and 3d, may be associated with user features that are more advanced than other levels. For example, a meter 10 may include a feature that displays a date and time indicator 40 that can display a date and time associated with either a home time zone or a local time zone, as shown in FIG. 3a. Additionally, an "advanced" level may include a feature that allows a user to store an even greater number of concentration readings 42. In some embodiments, at least 400 concentration readings 42 may be stored. For example, as shown in the embodiment in FIG. 3c, 480 readings may be stored. Other user features may allow a user to calculate multiple multi-day averages 44 of concentration readings, such as 7-day, 14-day, and 30-day averages, as shown in FIG. 3b. As in the "intermediate" mode, to indicate that the averaging feature is in use, an averaging icon 26, such as an "A", may be displayed on the meter 10. Other features may allow a user to calculate morning, afternoon and evening averages (not shown). Similar to the "intermediate" level user features, all of the readings and averages may be downloaded via the computer data interface 60 (see FIG. 4).

Figure 3D:
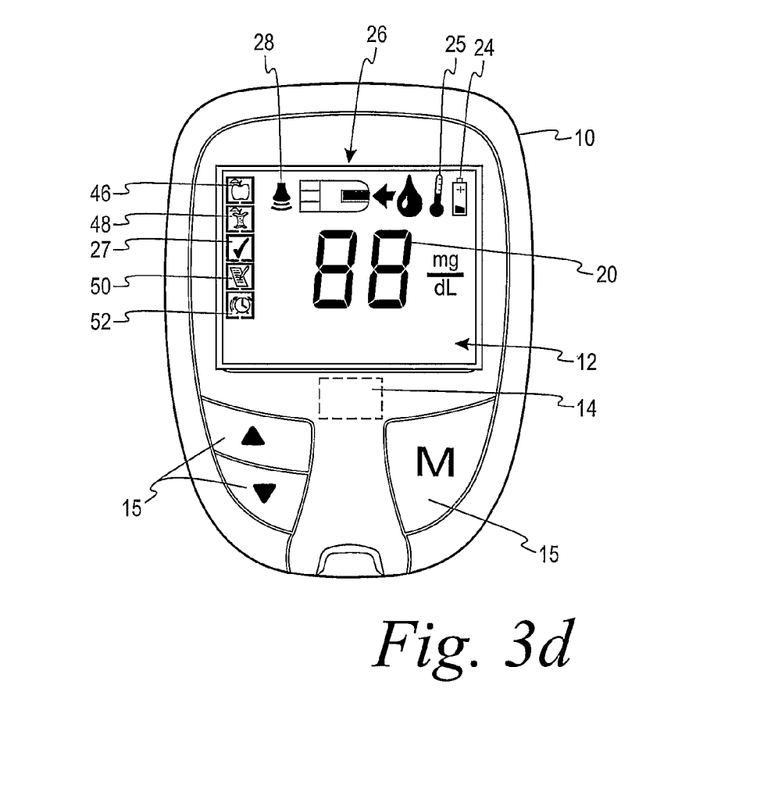

Other user features that may be included in an "advanced" level may include testing alarms 52 for indicating when it is necessary for a user to take a blood glucose reading. The testing alarm 52 times may be preprogrammed via the user interface or may be inputted by a user. In addition to a testing alarm 52, some embodiments of the present invention may include various markers which may be activated to associate certain events with certain concentration readings. These markers allow a user to compare the marked concentration reading with other readings taken under the same or similar conditions. Some examples of markers are shown in FIG. 3d. A pre-meal marker 46 and a post-meal marker 48 can be used to label those concentration readings that are taken before and after a meal, respectively. Some other examples include a logbook marker 50 that allows a user to mark a concentration reading 22 and associate the concentration reading 22 with notes and/or comments related to that particular concentration reading 22. These notes may relate to some condition or event that occurred before the concentration reading 22 was taken that may be helpful to a doctor who is monitoring a user's glucose levels. Some other markers may include exercise markers, medication markers, fasting-time markers, and illness markers. It is contemplated that many other markers may be used with the present invention. All of these markers may be used to label concentration readings so that a user or doctor can associate concentration readings with certain activities that may occur during a day and that may influence the concentration readings.

It is contemplated that other user features may be available in an "advanced" mode in addition to the features listed herein. Such "advanced" features may allow users to calculate readings associated with other analytes, such as hematocrit readings. Other features may include notifying a user when high or low readings are taken. With this feature, the meter 10 may display a set of high readings and a set of low readings such that the user is able to view the range of readings and can adjust his or her diet, activities, etc. accordingly. Moreover, the high and low readings can be saved in the memory device for later retrieval by the user's doctor for further evaluation. It is contemplated that other user features may be available in an "advanced" mode, such as one or more of the features described herein with respect to the "beginner" and "intermediate" modes.

In some embodiments, the glucose meter may be initially configured at a "beginner" level so that even the most technically challenged user will have a simple, straightforward glucose meter that is ready to use. The more advanced levels may be selected using a setup mode that can be activated using the user input mechanism 15. Once activated, a user can use the user input mechanism 15 to set the time, date and other user-configurable settings. In other embodiments, the glucose meter may be initially configured at an "intermediate" or "advanced" level. In yet other embodiments, the user may initially scroll through the predefined levels and select the one that most closely meets his or her needs.

Some commercially available meters, such as those that are manufactured and/or sold by Bayer Healthcare LLC of Tarrytown, N.Y., may be redesigned to incorporate the present invention, such as the Ascensia® CONTOUR® Blood Glucose Monitoring System and the Ascensia® BREEZE® Blood Glucose Monitoring System. It is contemplated that other meters, in addition to the ones listed above, may incorporate the present invention as described herein.

The present invention thus allows a user to select certain predefined levels of user features according to his or her preferences, needs and abilities. Less sophisticated users may choose a level having fewer, simpler features, i.e., the "beginner" or "intermediate" levels, while more sophisticated users may choose a level offering additional features having more complex functions and capabilities. A meter having the predefined levels as described herein can appeal to multiple user types and a single user can select other levels as his or her needs and/or understanding of the features increases.

Alternative Embodiment A

A meter adapted to determine and store an analyte concentration reading, the meter comprising:

a display adapted to display information to a user of the meter;

an interface that controls the display for the user, the interface having a plurality of predefined levels of user features that are adapted to be selected by the user; and at least one user input mechanism adapted to allow the user to select one of the plurality of predefined levels of user features.

Alternative Embodiment B

The meter according to Alternative Embodiment A, further comprising a memory device adapted to store the selected predefined level.

Alternative Embodiment C

The meter according to Alternative Embodiment A, wherein the analyte is glucose.

Alternative Embodiment D

The meter according to Alternative Embodiment A, wherein the plurality of predefined levels includes at least three predefined levels.

Alternative Embodiment E

The meter according to Alternative Embodiment D, wherein a first predefined level is adapted to include a user feature for saving at least twenty concentration readings.

Alternative Embodiment F

The meter according to Alternative Embodiment D, wherein a second predefined level is adapted to include user features for saving at least 200 concentration readings, for calculating a 14-day average, for displaying a date and time and for downloading the concentration readings via a computer data interface.

Alternative Embodiment G

The meter according to embodiment D, wherein a third predefined level is adapted to include user features for saving at least 400 concentration readings, for calculating multi-day averages of concentration readings, for displaying a date and time for at least two time zones, for downloading the concentration readings via a computer data interface, for displaying at least one high concentration reading and at least one low concentration reading, for providing a test-time alarm and for marling a concentration reading.

Alternative Process H

A method for using a meter adapted to determine and store an analyte concentration reading, the meter having a display adapted to display information to a user, the method comprising the acts of:

displaying information on the display via a user interface, the interface having a plurality of predefined levels of user features;

selecting one of the plurality of predefined levels; and displaying the user features associated with the selected predefined level.

Alternative Process I

The method according to Alternative Process H, further comprising storing the selected predefined level.

Alternative Process J

The method according to Alternative Process H, wherein the analyte is glucose.

Alternative Process K

The method according to Alternative Process H, wherein the plurality of predefined levels includes at least the predefined levels.

Alternative Process L

The method according to Alternative Process K, wherein a first predefined level is adapted to include a user feature for saving at least twenty concentration readings.

Alternative Process M

The method according to Alternative Process K, wherein a second predefined level is adapted to include user features for saving at least 200 concentration readings, for calculating a 14-day average, for displaying a date and time and for downloading the concentration readings via a computer data interface.

Alternative Process N

The method according to Alternative Process K, wherein a third predefined level is adapted to include user features for saving at least 400 concentration readings, for calculating multi-day averages of concentration readings, for displaying a date and time for at least two time zones, for downloading the concentration readings via a computer data interface, for displaying at least one high concentration reading and at least one low concentration reading, for providing a test-time alarm and for marking a concentration reading.

Alternative Embodiment O

A meter adapted to determine and store an analyte concentration reading, the meter comprising:
a display adapted to display information to a user of the meter;
an interface that controls the display for the user, the interface having at least three predefined levels of user features that are adapted to be selected by the user; and
at least one user input mechanism adapted to allow the user to select one of the at least three predefined levels of user features.

Alternative Process P

A method for using a meter adapted to determine and store an analyte concentration reading, the meter having a display adapted to display information to a user, the method comprising the acts of:
displaying information on the display via a user interface, the interface having at least three predefined levels of user features;
selecting one of the at least three predefined levels; and
displaying the user features associated with the selected predefined level.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention. as defined by the appended claims.

The invention claimed is:

1. A meter for determining and storing at least one analyte concentration reading, the meter comprising:
a display adapted to display information to a user of the meter;
an interface adapted to control the display for the user, the interface having a plurality of predefined levels of user features selectable by the user, the plurality of predefined levels including at least three predefined levels, at least one of the three predefined levels including user features adapted to save at least 200 concentration readings, calculate a 14-day average, display a date and time, and download the concentration readings via a computer data interface; and
at least one user input mechanism adapted to allow the user to select at least one of the plurality of predefined levels of user features.

2. The meter of claim 1, wherein at least a second one of the three predefined levels includes user features adapted to save at least 400 concentration readings, calculate multi-day averages of concentration readings, display a date and time for at least two time zones, download the concentration readings via a computer data interface, display at least one high concentration reading and at least one low concentration reading, provide a test-time alarm, and mark a concentration reading.

3. The meter according to claim 1, further comprising a memory device adapted to store the selected predefined level.

4. The meter according to claim 1, wherein the analyte is glucose.

5. A method for using a meter adapted to determine and store at least one analyte concentration reading, the meter having a display adapted to display information to a user, the method comprising:
displaying information on the display via a user interface, the interface having a plurality of predefined levels of user features, the plurality of predefined levels including at least three predefined levels, at least one of the three predefined levels including user features adapted to save at least 200 concentration readings, calculate a 14-day average, display a date and time, and download the concentration readings via a computer data interface;
selecting one of the plurality of predefined levels; and
displaying the user features associated with the selected predefined level.

6. The method of claim 5, wherein at least a second one of the three predefined levels includes user features adapted to save at least 400 concentration readings, calculate multi-day averages of concentration readings, display a date and time for at least two time zones, download the concentration readings via a computer data interface, display at least one high concentration reading and at least one low concentration reading, provide a test-time alarm, and mark a concentration reading.

7. The method according to claim 5, wherein the analyte is glucose.

* * * * *